United States Patent [19]

Johnson et al.

[11] Patent Number: 5,039,431
[45] Date of Patent: Aug. 13, 1991

[54] MELT-BLOWN NONWOVEN WIPER

[75] Inventors: Malcolm L. Johnson, East Point; Tracey A. Burbank, Eatonton; Mark D. Strickland, Woodstock, all of Ga.

[73] Assignee: Kimberly-Clark Corporation, Neenah, Wis.

[21] Appl. No.: 454,098

[22] Filed: Dec. 19, 1989

Related U.S. Application Data

[62] Division of Ser. No. 357,397, May 26, 1989, Pat. No. 4,904,521.

[51] Int. Cl.⁵ .................................................. D04H 1/16
[52] U.S. Cl. ................................... 264/113; 156/62.8; 156/286; 428/284; 428/903; 264/6
[58] Field of Search ........................... 264/109, 113, 6; 156/62.8, 286; 428/903, 284

[56] References Cited

U.S. PATENT DOCUMENTS

| Re. 31,885 | 5/1985 | Meitner | 252/91 |
| 3,795,571 | 3/1974 | Prentice | 161/148 |
| 3,849,241 | 11/1974 | Butin et al. | 161/169 |
| 4,165,352 | 8/1979 | Volhman | 264/113 |
| 4,436,780 | 3/1984 | Hotchkiss et al. | 428/198 |
| 4,666,763 | 5/1987 | Hing et al. | 428/903 |
| 4,714,647 | 12/1987 | Shipp et al. | 428/212 |
| 4,774,125 | 9/1988 | McAmish | 428/198 |

OTHER PUBLICATIONS

NRL Report 4364, V. A. Wente, E. L. Boone, D. C. Fluharty, May 1954.
NRL Report 5265, K. D. Lawrence, R. T. Lucas, J. A. Young, Feb. 1959.

Primary Examiner—James J. Bell
Attorney, Agent, or Firm—William D. Herrick

[57] ABSTRACT

There is disclosed a nonwoven wiper comprising a composite web made of a number of interbonded layers of meltblown thermoplastic fibers. The outer layers have average pore sizes greater than 20 microns and preferably greater than 40 microns for rapid pick up of liquid. The internal layers have average pore sizes between 10-20 microns for liquid holding capacity.

1 Claim, 1 Drawing Sheet

MELT-BLOWN NONWOVEN WIPER

This is a divisional application of Application Ser. No. 07/357,397, filed on May 26, 1989 U.S. Pat. No. 4,904,521.

BACKGROUND OF THE INVENTION

This invention relates generally to melt-blown materials, and more particularly concerns a melt-blown nonwoven wiper consisting of a composite web made up of layers of melt-blown fibers. The layers have different fiber and pore sizes resulting in a pore size distribution across the thickness or Z-direction of the web. The pore size distribution is tailored to optimize liquid pick up rate and liquid holding capacity of the wiper.

The melt-blown nonwoven wipers are well known in the art and find utility as disposable industrial wipers in numerous manufacturing and maintenance facilities where personnel find it necessary to wipe up oil, grease, and water from a variety of surfaces. Such nonwoven wipers generally consist of a web of melt-blown thermoplastic fibers. One such wiper made of melt-blown polypropylene fibers is sold by the assignee of the present invention under the trademark Kimtex.

Melt-blown nonwoven wipers have the advantage over cloth wipers of being cost effectively disposable and providing similar wiping characteristics to cloth. Particularly, all industrial wipers must be able to quickly pick up spilled liquids. both oil based or water based, and leave a clean streak free surface. In addition, the wipers must have a sufficient capacity to hold such liquids within the wiper structure until it is desired to remove the liquids by pressure such as by wringing.

As a practical matter, a nonwoven industrial wiper will be judged in terms of performance with respect to traditional nondisposable, woven cotton shop towels. In that regard, it is necessary to design a nonwoven industrial wiper so that its performance characteristics approach those of the traditional woven shop towel while providing cost effective disposability of the nonwoven industrial wiper. In the past, nonwoven industrial wipers have not been able to provide the same desired performance as woven shop towels, particularly, in terms of the rate of pick up of oil and water and the holding capacity for both oil and water. Moreover, such deficiencies of nonwoven industrial wipers are particularly troublesome because there appears to be an inverse relationship between the holding capacity of the nonwoven industrial wipers and the rate of pick up. In other words, in order to increase holding capacity, it has in the past been thought that it was necessary to sacrifice the rate of pick up. Likewise, in order to improve rate of pick up, it was thought necessary to sacrifice some holding capacity.

SUMMARY OF THE INVENTION

It is therefore an object of the present invention to provide a melt-blown thermoplastic web for use as an industrial wiper which has improved oil and water capacity as well as an improved rate of pick up for both oil and water.

The foregoing objective is obtained by producing a composite web comprising interbonded layers of melt-blown thermoplastic fibers. The composite web has a pore size distribution across its thickness or Z-direction with at least one outer layer having large pores with an average pore size greater than 20 microns and preferably greater than 40 microns. Such an outer layer with its large average pore size will quickly pick up liquids from a surface. In order to maintain and improve capacity, the internal layers of the composite web have pores with an average size between 10 microns and 20 microns. Such a composite web provides rapid pick up as a result of the large pore sizes which make up the outer layers, while the internal layers with their relatively smaller pore sizes provide holding capacity.

In order to produce such an improved industrial wiper, the wiper is produced on a multi-bank melt-blowing machine wherein a number of layers are sequentially laid down with the melt-blowing parameters of each layer adjusted to achieve the desired large or relatively smaller pore size to produce the improved industrial wiper.

Particularly, it has been found that a composite web having outer layers with pores having an average size greater than 20 microns and preferably greater than 40 microns and internal layers having pores with an average size of from 10 to 20 microns provides both improved rate of pick up and improved capacity over a melt-blown web which has a uniform pore size distribution in the Z-direction.

DETAILED DESCRIPTION OF THE INVENTION

While the invention will be described in connection with a preferred embodiment and procedure, it will be understood that we do not intend to limit the invention to the embodiment or procedure. On the contrary, we intend to cover all alternatives, modifications, and equivalents as may be included within the spirit and scope of the invention as defined by the appended claims.

Figure 1:
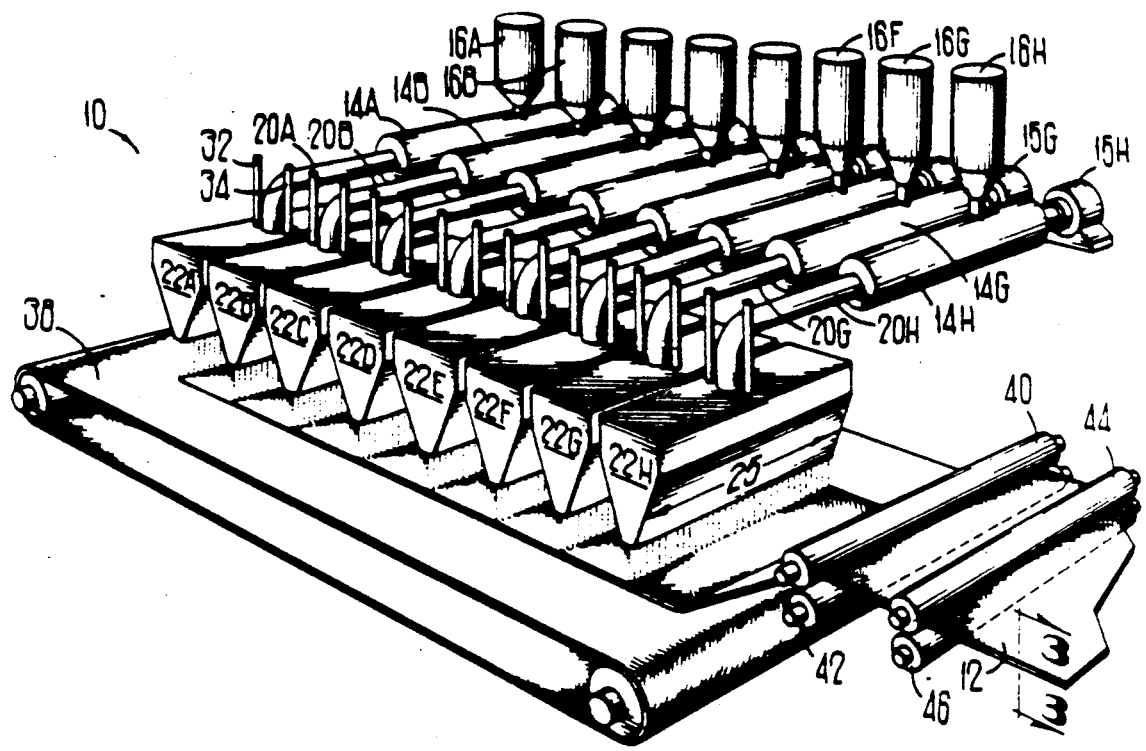
FIG. 1 is a schematic diagram showing machinery for producing the melt-blown nonwoven wiper of the present invention.
Figure 3:
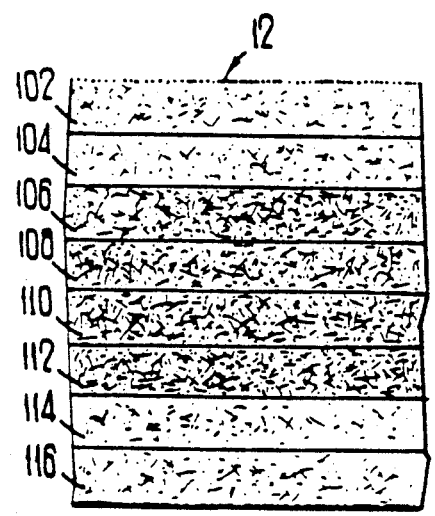
FIG. 3 is a schematic cross-sectional representation of the melt-blown nonwoven wiper of the present invention.

Turning to FIG. 1 there is shown a web forming machine 10 for forming a melt-blown web 12 made up of a number of layers (102, 104, 106, 108, 110, 112, 114, and 116 in FIG. 3) of melt-blown fibers. The machine 10 includes eight identical extruders 14A-H with corresponding hoppers 16A-H for receiving thermoplastic resin pellets. The extruders 14A-H include internal screw conveyors which are driven by motors 15A-H. The extruders 14A-H are heated along their lengths to the melting temperature of the thermoplastic resin pellets to form a melt. The srew conveyors driven by motors 15A-H, force the thermoplastic material through the extruders into attached delivery pipes 20A-H which are connected to die heads 22A-H, each having a die width 25.

Figure 2:
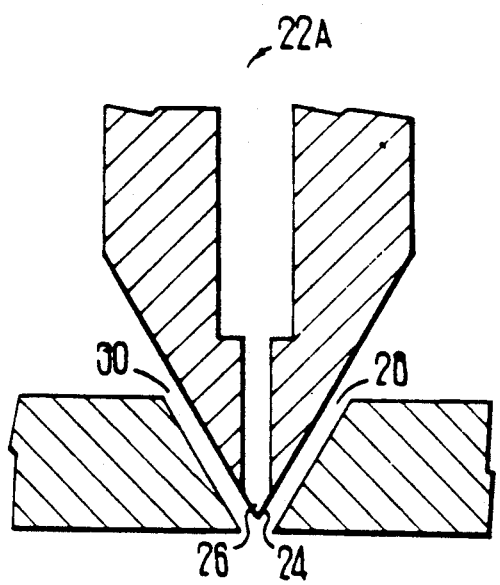
FIG. 2 is a cross-sectional diagram of a die head used in connection with carrying out the melt-blown process of the present invention.

Die head 22A, for example, is shown in cross-section in FIG. 2 and comprises a die tip 24 which has a die opening or orifice 26 therein. Hot fluid, usually air, is supplied to the die tip via pipes 32 and 34 (FIG. 1) which terminate in channels 28 and 30 adjacent outlet 26 of the die tip.

As the thermoplastic polymer exits the die tip at the opening 26 for each die head, the high pressure air attenuates and breaks up the polymer stream to form fibers at each die head which fibers are deposited in layers on a moving foraminous belt 38 to form the composite layered web 12. A vacuum is drawn behind the foraminous belt 38 to draw the fibers onto the belt 38 during the process of melt-blowing. Separate vacuum chambers behind the foraminous belt may be provided for each die head 22A-H. Once the fiber layers have been deposited on the moving belt 28 by the multiple die heads 22A-H, the web 12 is drawn from the belt 38 by withdrawal rolls 40 and 42. Embossing rolls 44 and 46 engage the web 12 after the withdrawal rolls to emboss the web with a pattern thereby improving the drape stiffness of the composite web 12.

The foregoing description of the melt-blowing machine 10 is generally conventional and well known in the art as demonstrated by NRL Report 4364, "Manufacture of Super-Fine Organic Fibers", by V. A. Wendt, E. L. Boon, and C. D. Fluharty; NRL Report 5265, "An Improved Device for the Formation of Super-Fine Thermoplastic Fibers", by K. D. Lawrence, R. T. Lukas,, and J. A. Young; and, U.S. Pat. No. 3,849,241, issued Nov. 19, 1974, to Buntin, et al.

The characteristics of the melt-blown web 12 can be adjusted by manipulation of the various process parameters used for each extruder and die head in carrying out the melt-blown process on the melt-blowing machine 10. The following parameters can be adjusted and varied for each extruder and die head in order to change the characteristics of the resulting melt-blown fiber layer:

1. Type of Polymer,
2. Polymer throughput (pounds per inch of die width per hour-PIH),
3. Polymer melt temperature (°F.),
4. Air temperature (°F.),
5. Air flow (standard cubic feet per minute, SCFM, calibrated for a 20 inch wide die head),
6. Distance from between die tip and forming belt (inches), and
7. Vacuum under forming belt (inches of water).

By controlling the process parameters for manufacture of melt-blown webs, webs can be constructed having more or less open web structure. For webs of the same basis weight, we have found that a web with a more open web structure resulting from larger fibers and pore sizes is able to more quickly pick up liquids from a surface, but that same open web has a lower capacity than a closed web (i.e. smaller fibers and smaller pores). Consequently, in order to produce a superior wiper, we have found that a composite web having outer layers of open structure (i.e. large fibers and large pore sizes) and internal layers of less open structure (i.e. smaller fibers and smaller pore sizes) produces a superior nonwoven industrial wiper having quick pick up rates as a result of the outer open structured layers with high capacities as a result of the internal layers of more closed structure.

In connection with initial work on the present invention, eleven melt-blown single layer webs of polypropylene fibers were manufactured having various average pore sizes ranging from an average pore size of 12.81 microns to an average pore size of 23.43 microns. The pore size for each sample web was determined using Coulter Porometer. For each sample, the bulk in inches was measured in accordance with an Ames Tester Model 3223 from B. C. Ames Company of Waltham, Mass. and recorded. Likewise, the basis weight in grams per square meter ($g/m^2$) was measured in accordance with Federal Test Method 191A, Method 5040 and 5041, and the results were recorded for each sample. Each sample was then tested for water pick up rate, water capacity, oil pick up rate, and oil capacity. The water and oil pick up rates measured in seconds, were determined in accordance with TAPPI Standard Method T432 su-72 except that 0.1 ml of white mineral oil was used as the test liquid for oil, three separate drops of test liquid were used on each sample, and five rather than ten samples were tested. The water and oil capacities measured in grams per square foot ($g/ft^2$) were determined in accordance with Federal Specification No. UU-T-595C.

From the data for the samples, it appeared that for the oil, there was a very strong correlation between the pick up rate and the average pore size as well as the capacity and the average pore size. For large average pore sizes, the oil pick up rate was highest (time in seconds lowest) and the oil capacity was lowest. For smaller average pore sizes, the oil pick up rate was lowest (time in seconds being highest) and the oil capacity was highest. The data for water pick up rates and water capacity were more ambiguous because the performance was in some degree masked by uneven application of surfactant on the polypropylene web. In general, however, the water pick up rates were higher for larger pore size webs, and the water capacity was higher for small pore size webs.

In addition, each of the eleven webs was characterized by process parameters used on the melt-blowing machine for making the web. The parameters included polymer throughput, air temperature, melt temperature, and air flow. Based on the average pore sizes and the process parameters, it was found that polymer throughput had the greatest effect on the fiber and pore size of the melt-blown web followed in order by air flow, air temperature, and melt temperature.

EXAMPLE 1

In order to further study the effect of pore size, eight large pore base sheets with an average basis weight of 0.4 $oz/yd^2$ were produced with the polymer throughput set at 4.8 lbs./in/hr, the maximum upper machine limitation. Polypropylene pellets supplied under the designation PF015 by Himont, Himont USA, Inc., 3 Little Falls Center, 2001 Centerville Road, P.O. Box 15439, Wilmington, Del. 19850-5439 were used. Air temperature, melt temperature, air flow, forming distance, and under wire vacuum were varied in accordance with the following table:

TABLE 1

| Sample ID | Polymer Throughput (PIH) | Air Temp. (°F.) | Melt Temp. (°F.) | Air Flow (SCFM) | Forming Distance (in) | Vacuum (in of $H_2O$) |
|---|---|---|---|---|---|---|
| 1 | 4.8 | 395 | 472 | 300 | 18.0 | 2.5 |
| 2 | 4.8 | 396 | 473 | 300 | 19.5 | 2.5 |
| 3 | 4.8 | 397 | 541 | 150 | 18.0 | 2.0 |
| 4 | 4.8 | 397 | 541 | 250 | 18.0 | 2.0 |
| 5 | 4.8 | 393 | 540 | 350 | 18.0 | 3.0 |
| 6 | 4.8 | 396 | 539 | 350 | 19.5 | 3.0 |
| 7 | 4.8 | 554 | 539 | 350 | 19.5 | 3.0 |
| 8 | 4.8 | 554 | 540 | 350 | 18.0 | 3.0 |

The eight large pore sample sheets produced in accordance with the process parameters shown in the above Table 1 were then tested for bulk, drape stiffness (in accordance with ASTM Standard Test D 1388 in the machine direction (MD) and cross direction (CD) except a 1 in.×8 in. specimen was used instead of 1 in.×6 in.), water rate, water capacity, and average pore size. The results are shown in Table 2 below:

TABLE 2

| Sample ID | Bulk (in) | Drape Stiffness (cm) CD | Drape Stiffness (cm) MD | Water Rate (sec) | Water Capacity (%) | Water Capacity (g/m$^2$) | Average Pore Size |
|---|---|---|---|---|---|---|---|
| 1 | 0.020 | 2.11 | 1.45 | INST. | 438.36 | 82.59 | 25.85 |
| 2 | 0.021 | 1.76 | 1.64 | INST. | 448.63 | 84.27 | 20.10 |
| 3 | 0.019 | 1.57 | 1.40 | INST. | 542.24 | 83.64 | 30.15 |
| 4 | 0.014 | 2.01 | 2.64 | INST. | 751.38 | 104.86 | 25.85 |
| 5 | 0.013 | 1.19 | 1.26 | INST. | 933.05 | 105.69 | 25.85 |
| 6 | 0.016 | 1.82 | 2.32 | INST. | 717.55 | 110.14 | 21.35 |
| 7 | 0.012 | 1.65 | 1.81 | INST. | 739.75 | 88.62 | 21.35 |
| 8 | 0.014 | 1.96 | 1.88 | INST. | 985.98 | 106.62 | 16.75 |

As had been expected these samples showed an almost instantaneous water pick up rate of less than 0.5 seconds. The average water capacity for these samples was in the 400% to 900% range. The drape stiffness test confirmed that the large pore web structures were indeed somewhat stiffer than typical melt-blown webs of similar basis weight.

The eight webs were analyzed on a Coulter Porometer to determine the pores sizes that had been produced. The average pore sizes of the large pore melt-blown samples of Table 1 ranged from 40 to 80 microns as compared to a typical melt-blown which has average pore sizes in the range of 10 microns to 20 microns.

EXAMPLE 2

Subsequently, selected samples of the large pore webs of Example 1 were heat bonded to a standard absorbent core material to produce composite laminates. The laminates were then tested for oil and water pick up and oil and water capacities. For all cases but one, the laminates showed improved water rates over just the core material. All of the laminates showed much improved oil rates over just the core material. The data taken on capacity turned out to be inconclusive although all laminates showed increased capacity over the core material. The amount of increased capacity resulting from the laminated structure was partially masked by the increased bulk of the samples thereby rendering the test results ambiguous. As expected, a laminate made with six plies of all large pore melt-blown material had the fastest oil and water pick up rates but had the worst oil and water capacities of all of the laminates tested.

EXAMPLE 3

With the test results in hand, we have found that an improved industrial wiper can be formed using a multibank melt-blown machine 10 shown in FIG. 1. The melt-blown machine having eight separate melt-blowing heads 22A–H can sequentially produce a composite web 12 consisting of eight separate layers of melt-blown material, with each layer having its own fiber size and average pore size. By producing open structured layers with die heads 22A, 22B, 22G and 22H, the resulting composite web 12 have outer layers 102 and 104 on one side and outer layers 114 and 116 on the other side. The outer layers 102, 104, 114, and 116 have average pore sizes greater than 20 microns and preferably greater than 40 microns while the internal layers 106, 108, 110, and 112 have average pore sizes between 10 to 20 microns.

An improved industrial wiper in accordance with the present invention is made in accordance with the following manufacturing parameters:

TABLE 3

| | Outer Layers (102, 104, 114, 116) | Internal Layers (106, 108, 110, 112) |
|---|---|---|
| Polymer | Polypropylene (Himont PF015[?]) | Polypropylene (Himont PF015) |
| Polymer Throughput | 4.6 PIH | 3.8 PIH |
| Air Flow | 1400 SCFM | 2300 SCFM |
| Air Temperature | 500° F. | 590° F. |
| Melt Temperature | 590° F. | 590° F. |
| Forming Distance | 18" | 18" |
| Vacuum | 2.5 in. of H$_2$O at 54 psi | 2.8 in. of H$_2$O at 50 psi |

The improved industrial wiper made in accordance with the present invention, as in Example 3, has the following physical and performance characteristics:

TABLE 4

| Basis Weight (gr/m$^2$) | 68 |
|---|---|
| Bulk (inches) | .041 |
| CD Trap Tear (lbs) | 1.76 |
| CD Tensile (lbs) | 9.4 |
| MD Drape Stiffness (cm) | 5.9 |
| Oil Rate (sec) | 19.05 |
| Water Rate (sec) | 2.0 |
| Oil Capacity (%) | 401 |
| Water Capacity (%) | 611 |
| Average Pore Size (Outer layers) | 35 microns |
| Average Pore Size (Internal layers) | 15 microns |

The Trapezoid Tear Test was performed in conformance with ASTM Standard Test D 1117-14 except the load was calculated as the average of the first and highest peaks recorded, rather than the lowest and highest peaks recorded. The tensile strength was determined in accordance with Federal Test Method 191A.

In addition to polypropylene fibers, the present invention can be carried out using any thermoplastic resin that can be melt-blown to produce a coherent web.

We claim:

1. A process for forming a composite web having a basis weight and drape stiffness adapted for use as a nonwoven wiper comprising sequentially depositing and interbonding a number of layers of melt-blown thermoplastic fibers, one on top of the other, onto a collector wherein the forming parameters of each layer are controlled so that at least one outer layer has pores having an average size greater than 40 microns and at least one other layer has pores having an average size between 10 microns and 20 microns, and wherein said interbonding maintains the bulk of said composite.

* * * * *